(12) United States Patent
Ishikawa

(10) Patent No.: US 7,291,499 B2
(45) Date of Patent: Nov. 6, 2007

(54) TRANSFORMED CELL, METHOD OF SCREENING ANTI-AGING AGENT AND ANTI-AGING AGENT

(75) Inventor: Fuyuki Ishikawa, Room 201, Guranshitio-shimogamo 43, Shimogamomatsubaracho, Sakyo-ku, Kyoto-shi, Kyoto (JP) 606-0804

(73) Assignee: Fuyuki Ishikawa, Kyoto (JP)

( * ) Notice: Subject to any disclaimer, the term of this patent is extended or adjusted under 35 U.S.C. 154(b) by 294 days.

(21) Appl. No.: 10/484,033

(22) PCT Filed: Jul. 15, 2002

(86) PCT No.: PCT/JP02/07182

§ 371 (c)(1),
(2), (4) Date: Jan. 16, 2004

(87) PCT Pub. No.: WO03/008577

PCT Pub. Date: Jan. 30, 2003

(65) Prior Publication Data
US 2005/0288216 A1 Dec. 29, 2005

(30) Foreign Application Priority Data

Jul. 16, 2001 (JP) ............................ 2001-215576
Sep. 20, 2001 (JP) ............................ 2001-286412

(51) Int. Cl.
C12N 15/00 (2006.01)
C12N 5/06 (2006.01)
C12N 5/08 (2006.01)

(52) U.S. Cl. .................. 435/353; 435/357; 435/366; 435/364

(58) Field of Classification Search ................ 435/194, 435/252.3, 320.1, 6, 357, 360, 376, 366; 536/23.2
See application file for complete search history.

(56) References Cited

FOREIGN PATENT DOCUMENTS

| JP | 9-271395 A | 10/1997 |
|---|---|---|
| WO | 97/44467 A1 | 11/1997 |
| WO | WO 98/05761 A1 | 2/1998 |
| WO | WO 98/14592 A2 | 4/1998 |
| WO | 99/67283 A2 | 12/1999 |
| WO | WO 00/00491 A1 | 1/2000 |

OTHER PUBLICATIONS

Moriguchi, T. et al., A Novel Kinase Cascade Mediated by Mitogen-activated protein Kinase Kinase 6 and MKK3, J. Biol. Chem. (1996), vol. 271, No. 23, pp. 13675 to 13679.

Raingeaud, J. et al., MKK3- and MKK6- Regulated Gene Expression Is Mediated by the p38 Mitogen-Activated Protein Kinase Signal Transduction Pathway, Mol. Cell. Biol. (1996), vol. 16, No. 3, pp. 1247 to 1255.

(Continued)

Primary Examiner—Maryam Monshipouri
(74) Attorney, Agent, or Firm—Sughrue Mion, PLLC

(57) ABSTRACT

This invention provides a novel transformed cell useful in constructing an anti-aging agent screening system, a screening method which uses the same and an anti-aging agent, and it relates to a transformed cell in which a gene coding for (a) a protein capable of phosphorylating p38 protein, or (b) p38 protein, a mutant of p38 protein, a kinase domain of p38 protein, a kinase domain of p38 protein mutant or a fusion protein containing them is transformed into a normal cell, a screening method which uses this transformed cell and an anti-aging agent which uses a compound obtained by the screening method as the active ingredient.

10 Claims, 10 Drawing Sheets

OTHER PUBLICATIONS

Suh, Y. et al., Differential activation of mitogen-activated protein kinases by methyl methanesulfonate in the kidney of young and old rates, Mutatioon Research, Oct. 18, 2001 vol. 497, No. 1/2, pp. 11 to 18.

Mutsuhiro Takekawa et al., "A human homolog of the yeast Ssk2/Ssk22 MAP kinase kinase kinases, MTK1, mediates stress-induced activation of the p38 and JNK pathways", The EMBO Journal (1997) vol. 16, No. 16, pp. 4973-4982.

Igor Dozmorov et al., "Array-Based Expression Analysis of Mouse Liver Genes: Effect of Age and of the Longevity Mutant Prop1$^{df}$" Journal of Gerontology (2001) vol. 56A, No. 2, pp. B72-B80.

Xuechu Zhen et al., "Age-Associated Impairment in Brain MAPK Signal Pathways and the Effect of Caloric Restriction in Fischer 344 Rats" Journal of Gerontology (1999) vol. 54A, No. 12, pp. B539-B548.

Zhi-Qiang Xiao et al. "Induction of transcriptional activity of AP-1 and NF-kB in the gastric mucosa during aging" Am J. Physiol Gastrointest Liver Physiol (2000) vol. 278, No. 6, pp. G855-G865.

Eamonn O'Donnell et al., "Age-related impairment in LTP is accompanied by enhanced activity of stress-activated protein kinases: analysis of underlying mechanisms" European Journal of Neuroscience (2000) vol. 12, No. 1, pp. 345-352.

Chen-Hsiung Yeh et al., "Requirement for p38 and p44/p42 Mitogen-Activated Protein Kinases in RAGE-Mediated Nuclear Factor-kB Transcriptional Activation and Cytokine Secretion" DIABETES (2001) vol. 50, No. 6, pp. 1495-1504.

Michael M. Awad et al., "Growth Regulation via p38 Mitogen-activated Protein Kinase in Developing Liver" The Journal of Biological Chemistry (2000) vol. 275, No. 49, pp. 38716-38721.

Jun-o Deguchi et al., "Angiotensin II Stimulates Platelet-Derived Growth Factor-B Chain Expression in Newborn Rat Vascular Smooth Muscle Cells and Neointimal Cells Through Ras, Extracellular Signal-Regulated Protein Kinase, and c-Jun N-Terminal Protein Kinase Mechanism" Circulation Research (1999) vol. 85, No. 7 pp. 565-574.

Supplementary Partial European Search Report dated Jan. 3, 2005.

FIG. 2
PDL       42     61     42
PHOSPHORYLATED p38 
TOTAL p38 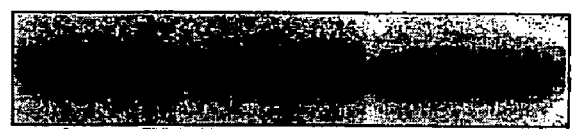

FIG. 7
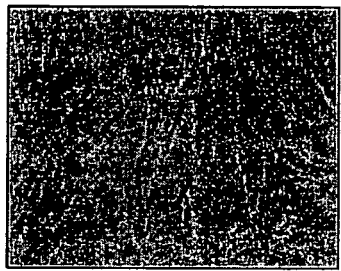  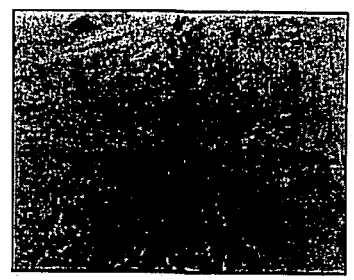
VECTOR   MKK6WT   MKK6EE

SEQUENCE LISTING

```
<160> NUMBER OF SEQ ID NOS: 2

<210> SEQ ID NO 1
<211> LENGTH: 28
<212> TYPE: DNA
<213> ORGANISM: Artificial Sequence
<220> FEATURE:
<223> OTHER INFORMATION: an artificially synthesized primer sequence

<400> SEQUENCE: 1
atagatatca tgtctcagtc gaaaggca                                    28

<210> SEQ ID NO 2
<211> LENGTH: 28
<212> TYPE: DNA
<213> ORGANISM: Artificial Sequence
<220> FEATURE:
<223> OTHER INFORMATION: an artificially synthesized primer sequence

<400> SEQUENCE: 2
aatgcggccg cttagtctcc aagaatca                                    28
```

TRANSFORMED CELL, METHOD OF SCREENING ANTI-AGING AGENT AND ANTI-AGING AGENT

This application is a National Phase entry of PCT/JP02/07182, filed Jul. 15, 2002, which claims priority to Japanese Application Numbers 2001-286412 filed Sep. 20, 2001 and 2001-215576 filed Jul. 16, 2001, respectively.

TECHNICAL FIELD

This invention relates to a novel transformed cell, a method for screening an anti-aging agent and an anti-aging agent.

BACKGROUND OF THE INVENTION

Cellular senescence is conditions under which a cell that should originally carry out cell growth cannot perform cell division in response to growth stimulation. A senescent cell is characterized by its large flat nucleus and a cellular senescence-specific β-galactosidase (senescence-associated β-galactosidase; SA-β-galactosidase) activity. In addition to morphological changes, the cellular senescent cell (senescent cell) shows characteristic changes in the gene expression patterns and the like.

There are many causes which trigger cellular senescence. For example, human normal fibroblast is a cell most generally used in the studies on cellular senescence. It is known that cellular senescence is induced when this is exposed to ionizing radiation or cultured under a high oxygen partial pressure. Also, in recent years, it has been reported that cellular senescence is rapidly induced after about 1 week when an activated oncognic RAS is expressed by force in human normal fibroblast.

However, the cellular senescence most thoroughly studied is a cellular senescence by the replicative life span (telomere-dependent) in which a normal cell reaches an aging cell after a finite number of cell divisions.

Since the cellular senescence generated by these different causes finally shows the same phenotype, it is considered that it occurs by the same molecular mechanism, but its details are not clear.

The cellular senescence based on the replicative life span is a phenomenon in which a normal cell becomes senescent cell after a certain number of cell divisions which vary depending on the kind of the cell. In the case of the most frequently used human normal fibroblast, a fetal cell shows an aging phenotype after about 60 to 80 times of cell division. This phenomenon was reported by Hayflick in 1962. However, it has been unclear for a long time that intracellular mechanism of the recording of the number of cell divisions. In recent years, it has been shown that DNA replication of the chromosomal terminal telomere is not complete due to the so-called "end replication problem", and the telomere length is shortened from about 50 to 200 base pairs per cell division, and that a cellular senescence is induced when this shortening reaches its threshold value. However, it is not clear that in what manner the cellular senescence occurs by the shortening of telomere length and whether or not its molecular mechanism is identical to cellular senescence caused by other causes.

On the other hand, MAPK (Mitogen-activated protein kinase) pathway is a cascade of protein kinases which exist in the cytoplasm and are activated by the intracellular and extracellular stimuli and thereby phosphorylate and activate downstream inactive protein kinases. The final target kinase MAPK phosphorylates and activates a specific transcription factor, and the cell responds to stimuli through the induction of the expression of a group of genes by the transcription factor.

The upstream kinase which phosphorylates the final target kinase MAPK is called MAPKK (MAPK2K), and the upstream kinase which phosphorylates the aforementioned MAPKK is called MAPKKK (MAPK3K). Two or more of the MAPK pathway are present, and MAPK, MAPKK and MAPKKK are known as each of them.

The classical MAPK pathway which was discovered and analyzed earliest in the history comprises Raf-Mek-Erk, and it responds to mainly extracellular stimuli, such as growth factor and the like and is activated via Ras. PD98059 is known as a specific inhibitor of Mek.

On the other hand, JNK (c-Jun N-terminal kinase) and p38 protein are known as the MAPK which is induced by cytokine of tumor necrosis factor (TNF) and the like that induce stress and apoptosis. Also, the MAPKK and MAPKKK of JNK and p38 protein are not single, but two or more of them are respectively known.

SB203580 is known as a compound which specifically inhibits the function of the p38 protein, and it is known that this compound inhibits production of inflammatory cytokines interleukin-1, interleukin-6, interleukin-8 or TNF and therefore is useful a therapeutic agent of inflammatory diseases (WO 97/33883).

DISCLOSURE OF THE INVENTION

Inventors of the present invention have conducted intensive studies on the cause of generating cellular senescence and found that the p38 MAPK pathway takes a direct role in the cellular senescence induced by two or more causes. Though the p38 MAPK pathway has been known as a MAPK pathway which induces stress or apoptosis as described in the above, its relationship with cellular senescence has been completely unknown.

In addition, the inventors of the present invention have also found based on this finding that when a gene coding for a protein which can activate p38 protein by its phosphorylation is introduced into a young cell, cellular senescence can be rapidly induced in the aforementioned juvenile cell.

The novel senescent cell obtained in this manner can be prepared within a short period of time in comparison with a natural senescent cell obtained via scores of times of natural division, and is markedly useful in constructing a screening system for anti-aging agents.

In addition, the inventors of the present invention have also and newly found that a known inhibitor for p38 protein shows anti-aging activity upon the aforementioned novel senescent cell and natural senescent cell. The invention is based on these findings.

An object of the invention is to provide a novel transformed cell useful in constructing a screening system for anti-aging agents, a screening system capable of using the same and an anti-aging agent.

More specifically, an object of the invention is to provide a novel transformed cell in which a gene coding for (a) a protein capable of phosphorylating p38 protein, or (b) p38 protein, a mutant of p38 protein, a kinase domain of p38 protein, a kinase domain of p38 protein mutant or a fusion protein containing them is transformed into a normal cell.

Also, another object of the invention is to provide a method for screening a compound, which comprises (1) a step for allowing a normal senescent cell or a normal cell introduced with a gene capable of inducing cellular senescence to contact with a substance to be tested, and (2) a step for analyzing an aging index in the cell.

In addition, still another object of the invention is to provide an anti-aging agent which comprises a compound obtained by the above screening method and an anti-aging agent which comprises a p38 protein inhibitor, as an active ingredients.

BRIEF DESCRIPTION OF THE DRAWINGS

FIG. 2 is a photograph which is a substitute for a drawing, showing a result of western blotting of each of the cell lysates shown in FIG. 1 using an anti-p38 antibody.

FIG. 7 is a photomicrograph which is a substitute for a drawing, showing the presence or absence of β-galactosidase activity in the transformed cell of the present invention.

BEST MODE FOR CARRYING OUT THE INVENTION

Figure 1:
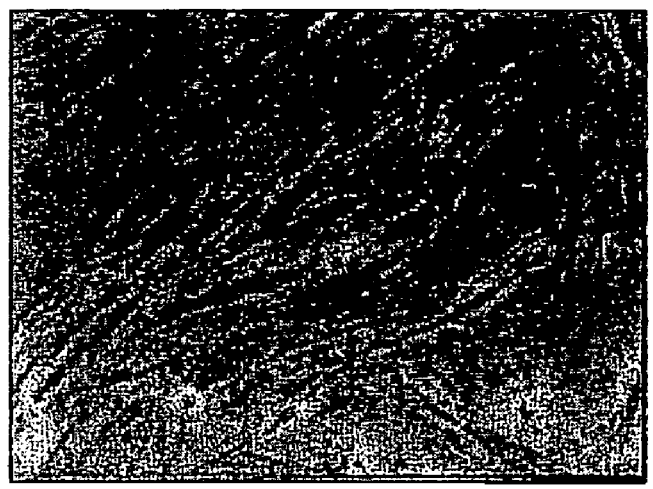
FIG. 1 is a photomicrograph which is a substitute for a drawing, showing the presence or absence of β-galactosidase activity in a juvenile cell and a senescent cell of human normal fibroblast WI-38.
Figure 1:
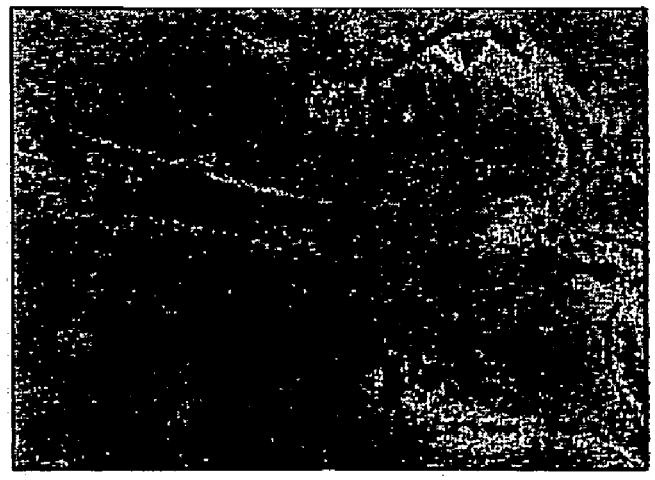

The present invention is described below in detail.

The transformed cell of the present invention can be obtained by introducing a gene coding for (a) a protein capable of phosphorylating p38 protein, or (b) p38 protein, a mutant of p38 protein, a kinase domain of p38 protein, a kinase domain of p38 protein mutant, or a fusion protein containing p38 protein, a mutant of p38 protein, a kinase domain of p38 protein or a kinase domain of p38 protein mutant, into a normal cell for transformation.

The term "p38 protein" as used herein means an enzyme of a monomer comprising a catalytic subunit of about 38,000 in molecular weight, which is one of the serine/threonine kinases and which belongs to the MAP kinase super family carrying out intracellular signal transduction. The host cell which can be used for preparing the transformed cell of the present invention, as well as the kinds of animal, and tissue from which it is derived and the number of cell divisions (namely, whether it is a young cell or senescent cell), is not particularly limited with the proviso that it is a cell which expresses p38 and from which cellular senescence can be induced by introducing a specified gene that can be used in the present invention (by further allowing an appropriate ligand to perform the reaction, if necessary).

As the host cell, for example, a mammal-derived cell is desirable, and a mammal-derived normal cell is more desirable. Examples of the mammal-derived normal cell include normal cells (e.g., a normal fibroblast, a normal keratinocyte, a normal mammary gland epithelial cell, a normal vascular endothelial cell and the like) derived from human, monkey, mouse, rat or hamster. Also as the aforementioned host cell, it is desirable to use a human-derived normal cell, and it is more desirable to use a human normal fibroblast. Examples of the human normal fibroblast include, WI-38 (ATCC, CCL-75), MRC-5 (ATCC, CCL-171), MBC-5 or IMR-90 (ATCC, CCL-186).

Also, the term "normal cell" means a cell under a state without cancerating, namely a cell having a finite life span.

Whether a cell is a young cell or a senescent cell can be expressed, for example, by a unit "PD".

The term "PD" as used herein is the abbreviation of population doublings and used as a unit which shows the number of cell divisions so far carried out by the cell. In this connection, since the number of cell divisions of each cell is generally different, PD is an average value in an individual cell in a cell group. For example, in the case of human fibroblast, the young cell generally means a cell of 0 to 50 PD (preferably a cell of 30 to 45 PD), and the senescent cell means a cell of 60 to 80 PD (preferably a cell of 60 to 65 PD).

As the host cell, both of the young cell and senescent cell can be used, but it is desirable to use a young cell capable of carrying out cell division (that is, a cell which is not reaching the replication life span and keeping the ability to actively perform cell division). This is because the senescent phenotype which can be rapidly obtained by the gene introduction shown below is greatly different from the phenotype before the gene introduction and can therefore be easily distinguished.

The introduction gene which can be used in preparing the transformed cell of the present invention is not particularly limited, so long as it is a gene which can encode (a) a protein capable of phosphorylating p38 protein (to be referred to as "p38 protein kinase" hereinafter), or (b) p38 protein, a mutant of p38 protein, a kinase domain of p38 protein, a kinase domain of p38 protein mutant or a fusion protein containing them (to be referred to as "p38 protein or a derivative thereof" hereinafter).

The p38 protein kinase (a) is not particularly limited with the proviso that it can phosphorylate p38 protein, but for example, (a1) MKK6 protein or MKK3 protein which is known as a MAPK that directly phosphorylates p38 protein in the p38 MAPK pathway;

(a2) an MKK6 protein mutant or an MKK3 protein mutant which is a natural or artificial mutant of the MKK6 protein or MKK3 protein (a1) and in which the activity to phosphorylate p38 protein is maintained or enhanced;

(a3) respective kinase domain of the MKK6 protein or MKK3 protein (a1) or respective kinase domain of the MKK6 protein mutant or MKK3 protein mutant (a2);

(a4) respective fusion protein of the MKK6 protein or MKK3 protein (a1) with a receptor ligand binding domain or respective fusion protein of the MKK6 protein mutant or MKK3 protein mutant (a2) with a receptor ligand binding domain; or (a5) respective fusion protein of respective kinase domain of the MKK6 protein or MKK3 protein with a receptor ligand binding domain or respective fusion protein of respective kinase domain of the MKK6 protein mutant or MKK3 protein mutant with a receptor ligand binding domain can be cited.

In this description, the term "phosphorylates p38 protein" as used herein means that it directly phosphorylates the p38 protein itself.

Examples of the aforementioned MKK6 protein or MKK3 protein (a1) include MKK6 protein or MKK3 protein derived from a mammal (e.g., human, monkey, mouse, rat or hamster), and it is desirable to use human or mouse MKK6 protein or MKK3 protein, it is more desirable to use human or mouse MKK6 protein and it is particularly desirable to use human MKK6 protein. For example, the region consisting of the amino acid residues of from the 53rd to 314th positions is the kinase domain in the case of the human MKK6 protein, and the region consisting of the amino acid residues of from the 35th to 269th positions is the kinase domain in the case of the human MKK3 protein.

Examples of the aforementioned MKK6 protein mutant or MKK3 protein mutant (a2) include a natural allele mutant of the MKK6 protein or MKK3 protein, a mutant prepared by artificially introducing a mutation through a known genetic engineering technique (e.g., site-specific mutagenesis; *Proc. Natl. Acad. Sci. USA*, 81: 5662-5666, 1984) and the like. More illustratively, a constitutive active type mutant in which the serine at the 207th position (Ser 207) and threonine at the 211th position (Thr 211) in the human MKK6 protein are respectively substituted with glutamic acid (Glu; E) (*Mol. Cell. Biol.*, 16: 1247-1255, 1996) can be exemplified.

Examples of the respective kinase domain (a3) of MKK6 protein, MKK3 protein or a mutant thereof include a human MKK6 protein fragment comprising a sequence consisting of the amino acid residues of from the 53rd to 314th positions in the human MKK6 protein (preferably a human MKK6 protein fragment consisting of a sequence consisting of the amino acid residues of from the 53rd to 314th positions in the human MKK6 protein), and a human MKK3 protein fragment comprising a sequence consisting of the amino acid residues of from the 35th to 269th positions in the human MKK3 protein (preferably a human MKK3 protein fragment consisting of a sequence consisting the amino acid residues of from the 35th to 269th positions in the human MKK3 protein).

The receptor in the respective fusion protein (a4) of the MKK6 protein or MKK3 protein or a mutant thereof with a receptor ligand binding domain, or respective fusion protein (a4) of respective kinase domain of the MKK6 protein or MKK3 protein or a mutant thereof with a receptor ligand binding domain is not particularly limited, so long as it is a receptor which, when the aforementioned fusion protein is expressed in a host cell, can activate another constituting component of the fusion protein (e.g., the MKK6 protein or MKK3 protein or a mutant thereof, or respective kinase domain of the MKK6 protein or MKK3 protein or a mutant thereof) through the activation of the receptor (that is, binding of a ligand to the receptor ligand binding domain). Examples of the receptor include a steroid receptor (e.g., an estrogen receptor), and for example, the ligand binding domain of a human estrogen receptor is a region consisting of the amino acid residues of from the 282nd to 595th positions of the human estrogen receptor.

Examples of the p38 protein or a derivative (b), include (b1) p38 protein;

(b2) a p38 protein mutant which is a natural or artificial mutant of the p38 protein (b1) and in which phosphorylation ability of p38 protein (that is, activity of p38 protein to phosphorylate its downstream protein) is maintained or enforced;

(b3) kinase domain of the p38 protein (b1) or kinase domain of the p38 protein mutant (b2);

(b4) respective fusion protein of the p38 protein (b1) or p38 protein mutant (b2) with a receptor ligand binding domain; and (b5) respective fusion protein of respective kinase domain (b3) of the p38 protein or p38 protein mutant with a receptor ligand binding domain.

Examples of the aforementioned p38 protein (b1) include p38 protein derived from a mammal (e.g., human, monkey, mouse, rat or hamster), and it is desirable to use human p38 protein. For example, the region consisting of the amino acid residues of from the 24th to 388th positions is the kinase domain in the case of the human p38 protein.

Examples of the aforementioned p38 protein mutant (b2) include a natural allele mutant of the p38 protein, a mutant prepared by artificially introducing a mutation through a known genetic engineering technique (e.g., site-specific mutagenesis) and the like.

Examples of the respective kinase domain (b3) of p38 protein or a p38 protein mutant include a human p38 protein fragment consisting of a sequence comprising the amino acid residues of from the 24th to 388th positions in the human p38 protein (preferably a human p38 protein fragment consisting a sequence consisting of the amino acid residues of from the 24th to 388th positions in the human p38 protein).

In the respective fusion protein (b4) of the p38 protein or a p38 protein mutant with a receptor ligand binding domain, or respective fusion protein (b5) of respective kinase domain of the p38 protein or a p38 protein mutant with a receptor ligand binding domain, the aforementioned receptor is not particularly limited, so long as it is a receptor which, when the aforementioned fusion protein is expressed in a host cell, can activate the p38 protein or a p38 protein mutant or respective kinase domain thereof, as another constituting component of the fusion protein, through the activation of the receptor (that is, binding of a ligand to the receptor ligand binding domain) Examples of the receptor include a steroid receptor (e.g., an estrogen receptor).

The method for introducing an introduction gene into a host cell in preparing the transformed cell of the present invention is not particularly limited and can be carried out using a conventionally known gene transduction method. Examples of the conventionally known gene transfer method include a method which uses a retrovirus (*Proc. Natl. Acad. Sci. USA*, 92: 9146-1950, 1995), a method in which an adenovirus is used, a DEAE-dextran method (*Nucleic Acids Res.*, 11: 1295-1308, 1983), a calcium phosphate-DNA coprecipitation method (*Virology*, 52:456-457,1973), a method which uses a commercially available transfection reagent (e.g., FuGENETM6 Transfection Reagent; manufactured by Roche Diagnostics), an electroporation (*EMBO J.*, 1: 841-845, 1982) and the like.

Since a gene coding for (a) a protein capable of phosphorylating p38 protein, the kinase domain thereof or a fusion protein containing them, or (b) p38 protein, the kinase domain thereof or a fusion protein containing them is introduced into the transformed cell of the present invention, cellular senescence is rapidly induced and its ability to carry out cell division is lost, whereas it kept the ability to carry out cell division actively before the aforementioned gene introduction.

In this connection, when a gene coding for a fusion protein with a receptor is used as the introduction gene, it is necessary for the induction of cellular senescence to allow the aforementioned receptor ligand to react upon the transformed cell.

Since the transformed cell of the present invention can be prepared within a markedly short period of time in comparison with a natural senescent cell obtained via scores of times or more of natural division, it is very useful in constructing a screening system for anti-aging agents.

The screening method for the anti-aging agent of the present invention includes (1) a step for allowing a normal senescent cell or a normal cell introduced with a gene capable of inducing cellular senescence to contact with a substance to be tested, and (2) a step for analyzing an aging index in the cell.

Although the cell which can be used in the screening method of the present invention is not particularly limited, so long as it is a cell capable of expressing p38, examples include a normal senescent cell, the aforementioned transformed cell and a transformed cell prepared by transforming a normal cell with a gene coding for (c) a protein positioned at the upstream of a MAPKK protein of the p38 pathway, a mutant of the protein positioned at the upstream of the MAPKK protein of the p38 pathway, the kinase domain of the protein positioned at the upstream of the MAPKK protein of the p38 pathway, or a fusion protein containing them, or (d) a protein which activates the p38 MAPK pathway or a fusion protein thereof.

The introduction gene which can be used for the preparation of the above transformed cells (c) and (d) is not particularly limited, so long as it is a gene which can encode (c) a protein positioned at the upstream of a MAPKK protein of the p38 pathway, a mutant of the protein positioned at the upstream of the MAPKK protein of the p38 pathway, the kinase domain of the protein positioned at the upstream of the MAPKK protein of the p38 pathway, or a fusion protein containing them, or (d) a protein which can activate the p38 MAPK pathway.

The protein positioned at the upstream of a MAPKK protein of the p38 pathway is not particularly limited, so long as it is a protein included in the p38 MAPK pathway, which can directly or indirectly phosphorylate the MAPKK protein of the p38 pathway, and its examples include proteins such as MAP3K, for example, MLK, MELK, ASK1, TAK1, and MTK1.

In addition, the MAPKK protein of the p38 MAPK pathway means a protein which phosphorylates p38 proteins such as MMK3, MMK6 and MMK4.

According to the present invention, the protein which activates the p38 MAPK pathway is not particularly limited, so long as it is a protein which does not belong to the p38 MAPK pathway but activates the p38 MAPK pathway, and its examples include a cytokine which activates the p38 MAPK pathway, MAPKKK kinases such as PAK1 and GCK, a protein contained in the classical MAPK pathway, mutants thereof and fusion proteins thereof, of which Raf and a fusion protein containing Raf can be cited as preferred examples.

Although they are not particularly limited, examples of the substance to be tested which can be used in the screening method of the present invention include commercially available compounds, various conventionally known compounds, a group of compounds obtained by the combinatorial chemistry techniques (*Tetrahedron*, 51: 8135-8173, 1995), culture supernatants of microorganisms, natural components derived from plants and marine organisms, animal tissue extracts, or compounds obtained by chemically or biologically modifying a compound selected by the screening method of the present invention.

According to the screening method of the present invention, the method for allowing a normal senescent cell or a normal cell introduced with a gene capable of inducing cellular senescence to contact with a substance to be tested is not particularly limited. However, for example, it can be carried out by adding the substance to be tested to a cultured medium of the aforementioned cell, by replacing a general medium (namely a medium which does not contain the substance to be tested) with a medium to which the substance to be tested was added in advance, or by adding the aforementioned cell to a medium to which the substance to be tested was added in advance. In this connection, when a gene coding for a fusion protein with a receptor is used as the transferring gene, it is necessary to induce cellular senescence prior to contacting with a substance to be tested, by allowing the aforementioned receptor ligand to act upon the transformed cell.

According to the screening method of the present invention, whether or not the aforementioned substance to be tested has an anti-aging activity can be judged by allowing a normal senescent cell or a normal cell introduced with a gene capable of inducing cellular senescence to contact with a substance to be tested and then observing change in an aging index in the aforementioned cell. In that case, it is desirable to jointly use, as a control, a normal senescent cell or a normal cell introduced with a gene capable of inducing cellular senescence, which is not contacted with the substance to be tested, because change in the aging index becomes more clear.

The term "anti-aging activity" as used herein means an anti-cellular aging activity, and the term "cellular senescence" means a cellular senescence due to the span of life of division, namely arrest of cell growth due to the span of life of cell division.

The aforementioned "anti-cellular aging activity" includes, for example, (1) a cellular replicative regeneration activity which regenerates the ability to perform cell division in a senescent cell which lost the cell division ability, and (2) a cellular senescence delaying activity which delays lowering rate of the cell division ability.

As the "aging index" which can be observed by the screening method of the present invention, it is not particularly limited so long as it is an index which shows the presence or absence, or the degree of cellular senescence, and examples include cell growth rate, a morphological change of cytoplasm, a change of an enzyme activity specific for cellular senescence, ratio of S phase cell and the like.

Specifically, in case that the cell growth rate is analyzed as the aging index, it can be judged that the aforementioned substance to be tested has the anti-aging activity when the cell growth rate after contacting with the substance to be tested becomes quick in comparison with a control (a aging cell which is not contacted with the substance to be tested).

In the case where a morphological change of cytoplasm is analyzed as the aging index, since the cytoplasm of a senescent cell generally takes a flat morphology, it can be judged that the aforementioned substance to be tested has the anti-aging activity when the flat cytoplasm becomes thin after its contact with the substance to be tested.

When a change of cellular senescent specific enzyme activity is analyzed as the aging index, β-galactosidase can be cited as the cellular senescence-specific enzyme.

In the case where the activity of a cellular senescence-specific enzyme (e.g., β-galactosidase) is reduced when contacted with a substance to be tested in comparison with a control (a senescent cell un-contacted with the substance to be tested), it can be judged that the aforementioned substance to be tested has the anti-aging activity.

In the case where the ratio of the S phase cell is analyzed as the aging index, since the ratio of S phase cell is generally high in the group of cells having active cell growth, when the ratio of S phase cell after contacting with the substance to be tested becomes high in comparison with a control (a senescent cell un-contacted with the substance to be tested), it can be judged that the aforementioned substance to be tested has the anti-aging activity.

Since a substance obtained by the screening method of the present invention has the anti-aging activity, namely a cellular replicative regeneration activity and/or a cellular senescence delaying activity, it is useful as the active ingredient of a cellular replicative regenerating agent or a cellular senescence delaying agent.

More specifically, the substance obtained by the screening method of the present invention has, for example, a p38 protein inhibitory activity or an activity to inhibit a cellular senescence signal transduction molecule which constitutes the cellular senescence signal transduction cascade at a down stream of the p38 protein.

The anti-aging agent of the present invention contains a p38 protein inhibitor as the active ingredient.

Various compounds are known as the p38 protein inhibitor, and its examples include the pyrazole compounds described in WO 95/31451, the pyrimidine compounds described in WO 97/33883 and the nitrogen-containing heterocyclic derivatives described in WO 98/27098.

As the conventionally known p38 protein inhibitors, examples include VX-745, VX-954, VX-702, SB203580 "4-[4-(4-fluorophenyl)-2-[4-(methylsulfinyl)phenyl]-1H-imidazol-5-yl]-pyridine", SB220025, RWJ-68354, RPR-68354, RPR-200765A, SC-XX906, HEP-689 (SB235699) and LL-Z-16402.

With regard to the p38 protein inhibitor as the active ingredient of the anti-aging agent of the present invention, preferred is a compound represented by formula (1)

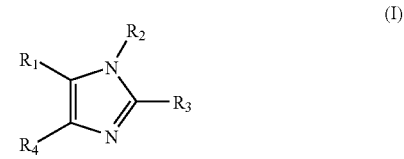

(I)

[wherein $R_1$ is a pyridyl group which is optionally substituted with one or two substituents independently selected from the group consisting of an alkyl group having from 1 to 4 carbon atoms, a halogen atom, an alkoxy group having from 1 to 4 carbon atoms, an alkylthio group having from 1 to 4 carbon atoms, an amino group and a mono- or di-alkyl (the number of carbon atoms of each alkyl moiety=1 to 6)amino group; $R_2$ is a hydrogen atom or an alkyl group having from 1 to 10 carbon atoms; $R_3$ is a phenyl group which is optionally substituted with one to three substituents independently selected from the group consisting of a halogen atom, an alkyl group having from 1 to 5 carbon atoms and $-(CH_2)_n Y$; $R_4$ is a phenyl group which is optionally substituted with one or two halogen atoms; Y is $-S(O)_m R_5$ or $-NR_6 R_7$; $R_6$ is a hydrogen atom or an alkyl group having from 1 to 10 carbon atoms, $R_7$ is a hydrogen atom, a benzyl group or an alkyl group having from 1 to 10 carbon atoms, or $R_6$ and $R_7$ together with the nitrogen atom to which they are bound may form a six-membered heterocyclic ring which optionally has an oxygen atom; $R_5$ is an alkyl group having from 1 to 10 carbon atoms; m is 0, 1 or 2; and n is 0 or 1].

In addition, with regard to the p38 protein inhibitor as the active ingredient of the anti-aging agent of the present invention, a compound of the aforementioned formula (1) wherein $R_1$ is an unsubstituted 4-pyridyl group, $R_2$ is a hydrogen atom, $R_3$ is a phenyl group substituted with $-S(O)_m R_5$ (wherein m is 1 or 2, and $R_5$ is an alkyl group having from 1 to 4 carbon atoms) and $R_4$ is a phenyl group substituted with a halogen atom is preferable; a compound wherein the substituent groups in $R_3$ and $R_4$ are bound at respective para-positions is more preferable; a compound wherein $R_3$ is a phenyl group substituted with $-SOR_5$ (wherein $R_5$ is an alkyl group having from 1 to 4 carbon atoms) and $R_4$ is a phenyl group substituted with a fluorine atom, a chlorine atom or an iodine atom is still more preferable; and a compound wherein $R_3$ is a phenyl group substituted with $-SOCH_3$ and $R_4$ is a phenyl group substituted with fluorine atom (namely SB203580) is particularly preferable.

A cellular replicative regenerating agent and a cellular senescence delaying agent are included in the anti-aging agent of the invention.

Examples of the cellular replicative regenerating agent include a wound treating agent which accelerates restoration of a wounded part; a preventing and/or treating agent for arteriosclerosis (particularly arteriosclerosis obliterans) wherein fallout and/or damage of vascular endothelial cells and the like could become the cause; a growth enhancer for tissue culture in regenerative treatment; a liver function recovering agent for hepatic cirrhosis and the like; an anemia improving agent for senile anemia and the like; an immunity recovering agent for senile immunodeficiency and the like; a mucosal epithelium function recovering agent for a chronic inflammatory gastrointestinal disease and the like; and a trichogenous agent, a hair tonic and the like.

Examples of the cellular senescence delaying agent include an arteriosclerosis preventing agent; a liver function reduction preventing agent for hepatic cirrhosis and the like; an anemia preventing agent for the aged and the like; an immunity reduction preventing agent for the aged and the like; a mucosal epithelium function reduction preventing agent for a chronic inflammatory gastrointestinal disease and the like; and an alopecia preventing agent, a hair tonic and the like.

The anti-aging agent of the invention can be prepared as a pharmaceutical composition in accordance with a general method using an appropriate pharmaceutical carrier. As the carrier, various carriers widely used in general drugs, such as an excipient, a binder, a disintegrator, a lubricant, a coloring agent, a taste masking agent, a flavoring agent, a surfactant and the like, can be used.

Dosage form of the anti-aging agent of the present invention is not particularly limited and can be optionally selected in response to the treating purpose. Examples include parenteral preparations such as injections, suppositories and external preparations (ointments, adhesive preparations and the like); aerosols and the like; and oral preparations such as tablets, powders, fine granules, granules, capsules, solutions, pills, suspensions, syrups and emulsions.

The aforementioned various drugs can be made into pharmaceutical preparations by general methods.

Examples of carriers which can be used in forming oral solid preparations such as tablets, powders, fine granules and granules include an excipient (lactose, sucrose, sodium chloride, glucose, starch, calcium carbonate, kaolin, crystalline cellulose, anhydrous dibasic calcium phosphate, alginic acid or the like); a binder (simple syrup, glucose solution, starch solution, gelatin solution; polyvinyl alcohol, polyvinyl ether, polyvinyl pyrrolidone, carboxymethylcellulose, shellac, methyl cellulose, ethyl cellulose, sodium alginate, gum Arabic, hydroxypropylmethylcellulose, hydroxypropylcellulose, water and/or ethanol solution thereof or the like); a disintegrator (starch, alginic acid, crosslinked polyvinyl pyrrolidone, crosslinked carboxymethylcellulose sodium, carboxymethylcellulose calcium, starch sodium glycolate or the like); a release controlling agent (a higher fatty acid, a higher aliphatic alcohol, cacao butter, a hydrogenated oil, a water-soluble polymer, a gastric polymer, an enteric polymer or the like); an absorption enhancing agent (a surfactant such as a quaternary ammonium salt, sodium lauryl sulfate or sorbitan monooleate); an adsorbing agent (starch, lactose, kaolin, bentonite, silicic acid anhydride, hydrous silicon dioxide, magnesium aluminometasilicate, colloidal silicic acid or the like); and a lubricant (purified talc, a stearate, a silicic acid, polyethylene glycol or the like).

If necessary, tablets can be made into general coating-treated tablets such as sugar coated tablets, gelatin coated tablets, gastric coated tablets, enteric coated tablets or water-soluble film coated tablets.

Capsules can be prepared by mixing with various carriers exemplified in the above and filling in hard gelatin capsules or soft capsules.

Liquid preparations may be water-soluble or oil-soluble suspensions, solutions, syrups or elixirs, and these can be prepared in accordance with a conventional known method using general additive agents.

When formed into a shape of suppositories, polyethylene glycol, cacao butter, lanolin, a higher alcohol, an ester of a higher alcohol, gelatin, hard fat or the like can be used as the carrier by adding an appropriate absorption enhancing agent thereto.

When formed into a form of injections, examples of useful carriers include a diluent (water, ethyl alcohol, Macrogol, propylene glycol or the like); a pH adjusting agent or buffer agent (citric acid, acetic acid, phosphoric acid, lactic acid or a salt thereof; sulfuric acid, sodium hydroxide or the like); and a stabilizing agent (sodium pyrosulfite, ethylenediaminetetraacetic acid, thioglycolic acid, thiolactic acid or the like). In addition, in this case, sodium chloride, glucose, mannitol or glycerol can be contained in the pharmaceutical preparation, in an amount sufficient for preparing an isotonic solution, and a general solubilization assisting agent, a soothing agent, a local anesthetic or the like can also be added.

When prepared into a form of ointments such as pastes, creams or gels, generally used bases, stabilizing agents, moistening agents, preservatives or the like are blended as occasion demands, and they can be mixed and made into a pharmaceutical preparation by a conventional method. Examples of the useful bases include white petrolatum, polyethylene, paraffin, glycerin, a cellulose derivative, polyethylene glycol, a dimethyl polysiloxane, a carboxyvinyl polymer, bentonite and the like. As the preservatives, parahydroxybenzoate ester and the like can for example be used.

When adhesive preparations are produced, the aforementioned ointments, creams, gels, pastes or the like can be coated on a general support by a conventional method. As the support, cotton; staple; woven or nonwoven fabric made of chemical fibers; and film such as soft vinyl chloride, polyethylene and polyurethane.

Although administration method of the anti-aging agent of the present invention is not particularly limited, it can be optionally administered orally or parenterally in response, for example, to the dosage form of the preparation, age, sex or other conditions of each patient or the degree of symptoms of the patient.

Clinical dose of the active ingredient of the anti-aging agent of the present invention can be optionally selected in response, for example, to the administration method, age and sex of each patient, form of the disease and other conditions, but it can be administered generally at a dose of from 1 to 2,000 mg per day per adult or dividing the daily dose into several doses.

EXAMPLES

The present invention is explained in detail based on reference examples and examples; however, they do not limit the scope of the present invention.

Reference Example 1

(1) Culturing of Cell

In this reference example, using a human normal fibroblast WI-38 (purchased from JCRB cell bank), confirmation was made on the differences in various aging indexes between active proliferating young cell which carried out 42 times of cell division after collection of the cell and its senescent cell after 61 times of cell division.

In this case, the aforementioned cells were cultured using 10% fetal calf serum (FCS)-containing DMEM (Dulbecco's modified Eagle's medium), and their sub-culturing was carried out at a ratio of 1:4. In that case, one sub-culturing was defined as 2 PD. According to this, a cell of from 30 to 40 PD was used as the young cell, and a cell of 60 PD as the senescent cell.

(2) Detection of Cellular Senescence-specific β-galactosidase (Senescence-associated β-galactosidase) Activity The cellular senescence-specific β-galactosidase activity was detected by the method of Dimri et al. (*Proc. Natl. Acad. Sci. USA*, 92: 9363-9363, 1995).

Specifically, young and senescent cells of the human normal fibroblast WI-38 were respectively washed with PBS and then fixed using 0.5% glutaraldehyde aqueous solution. After the fixation, the cells were soaked in a staining solution [prepared by dissolving 1 mg/ml of X-gal (5-bromo-4-chloro-3-indolyl-β-galactosidase), 5 mmol//L potassium ferrocyanide, 5 mmol//L potassium feriocyanide and 1 mmol//L magnesium chloride in phosphate buffered saline (PBS; pH 6.0)] and allowed to react at 37° C. for 5 hours or more.

Photomicrographs of the respective stained cells are shown in FIG. 1. In FIG. 1, the photograph (a) is a result of a young cell (42 times of division), and the photograph (b) is a result of a senescent cell (61 times of division). Each cell is stained blue in reality when it has the β-galactosidase activity, but it is shown in black in the monochrome photograph shown in FIG. 1.

As shown in FIG. 1, in the senescent cell [photograph (b)], the cytoplasm was flat in comparison with the young cell [photograph (a)], and the β-galactosidase activity was confirmed.

(3) Confirmation of Phosphorylated State of p38 Protein

In this reference example, the phosphorylated state of p38 protein in young and senescent cells of the human normal fibroblast WI-38 was confirmed by a Western blotting respectively using an antibody capable of detecting total p38 protein and another antibody capable of specifically detecting a phosphorylation type p38 protein (namely active type p38 protein) alone.

Specifically, young and senescent cells of the human normal fibroblast WI-38 (about 5×10$^6$ cells) cultured in the same manner as in Reference Example 1(1) were respectively dissolved in 0.1 ml of a buffer solution for dissolution [lysis buffer; 150 mmol//L sodium chloride, 0.5% NP-40, 50 mmol//L Tris-HCl (pH 7.5), 3 mmol//L EDTA, 3 mmol//L EGTA, 3 mmol//L glycerophosphate, 0.1μ//L Na$_3$VO$_4$, 1 μg/ml leupeptin and 1 mmol//L phenylmethanesulfonyl fluoride (PMSF)].

Subsequently, each extraction sample corresponding to 30 μg as the amount of protein was separated by an SDS polyacrylamide gel electrophoresis in the usual way and then transferred on a membrane (Immobilon-P membrane; manufactured by Millipore). After subjecting the membrane to a blocking treatment using a commercially available blocking agent (Block Ace; manufactured. by Dainippon Pharmaceutical), a primary antibody reaction and a secondary antibody reaction were carried out in order.

In this case, a rabbit anti-p38 antibody (manufactured by NEB; an antibody which reacts with all p38 proteins regardless of the presence or absence of phosphorylation) and a rabbit anti-phosphorylated p38 antibody (manufactured by NEB; an antibody which reacts with phosphorylated p38 protein but does not react with un-phosphorylated p38 protein) were used as the primary antibodies, and a horseradish peroxidase-labeled anti-rabbit IgG antibody (manufactured by Amersham) was used as the secondary antibody. Detection of the peroxidase activity was carried out using commercially available detection kit (manufactured by ECL; Amersham) and X-ray film (manufactured by Amersham).

The results are shown in FIG. 2. In this connection, a result of an anisomycin-treated young cell (42 PD) is also shown as a positive control. It is known that p38 protein is activated (phosphorylated) when a cell is treated with anisomycin. Anisomycin treatment of the cell was carried out prior to its lysis with the lysis buffer by culturing it for 30 minutes in DMEM containing 30 μmol//L anisomycin and 10% FCS.

In FIG. 2, lane 1 shows a result of the young cell (42 PD), lane 2 shows a result of the senescent cell (61 PD), and lane 3 shows a result of the positive control (namely, the young cell treated with anisomycin).

As shown in FIG. 2, difference in the expression of total p38 protein was not found among the three types of cells. On the other hand, the active type p38 protein was less in the young cell, increased in the anisomycin-treated young cell and more significantly increased in the senescent cell. Accordingly, it was shown that the p38 protein is activated by the cellular senescence of human normal fibroblast caused by its replicative life span.

Example 1

(1) Effect of p38 Protein Inhibitor in Human Normal Fibroblast

In the example, effect of a p38 protein inhibitor SB203580 was compared using the same young cell (42 times of division) and senescent cell (61 times of division) of the human normal fibroblast WI-38 used in Reference Example 1. Specifically, the same procedure of the following Example 2 (2) was repeated, except that a young cell (42 times of division) and a senescent cell (61 times of division) of the human normal fibroblast WI-38 cultured in the same manner in Reference Example 1(1) were used instead of the transformed cell.

Figure 3:
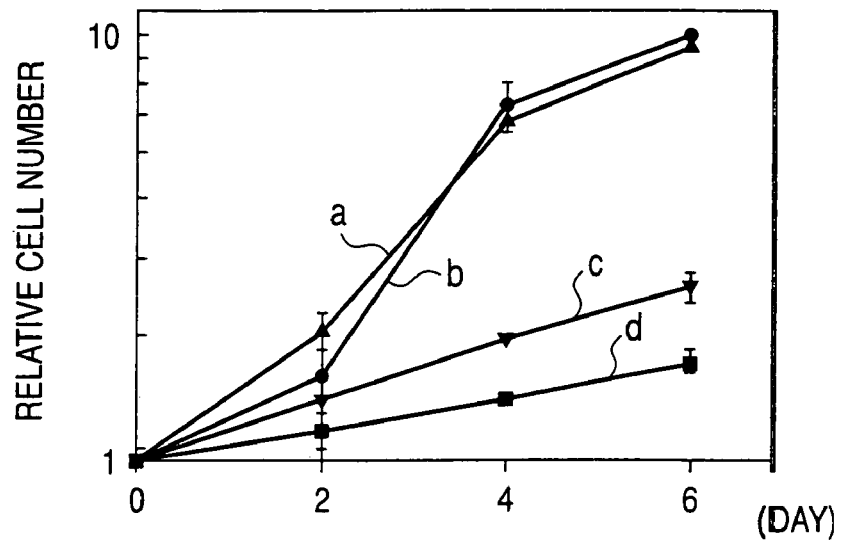
FIG. 3 is a graph showing cell growth curves of a juvenile cell and a senescent cell of human normal fibroblast WI-38 in the presence or absence of a p38 protein inhibitor, SB203580.

The results are shown in FIG. 3. In FIG. 3, the polygonal line a is cell growth curve of the young cell in the presence of SB203580, the polygonal line b is cell growth curve of the young cell in the absence of SB203580, the polygonal line c is cell growth curve of the senescent cell in the presence of SB203580 and the polygonal line d is cell growth curve of the senescent cell in the absence of SB203580. The symbol "+SB" in FIG. 3 means that it was treated with 10 μmol//L of SB203580.

Also, the ratio of S phase cells in each treated group was determined by FACS analysis in accordance with the procedure described in the following Example 2(3-a), and the results shown in FIG. 4. The symbol "+" in FIG. 4 means that it was treated with 10 μmol//L of SB203580.

In addition, cell morphology and β-galactosidase activity in each treated group were analyzed in accordance with the procedure described in Reference Example 1(2).

Figure 4:
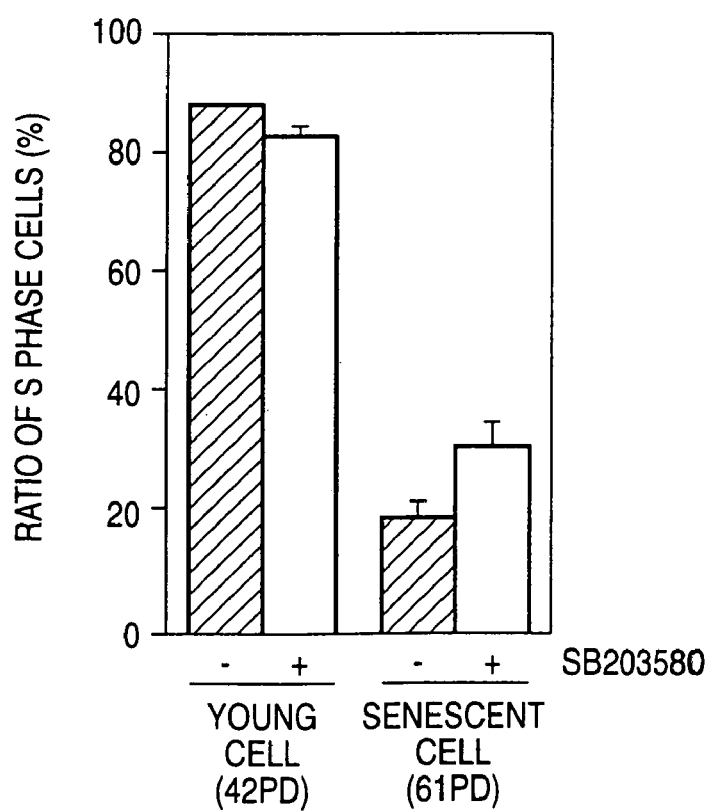
FIG. 4 is a graph showing the ratio of S phase cell in a juvenile cell and a senescent cell of human normal fibroblast WI-38 in the presence or absence of a p38 protein inhibitor, SB203580.

The young cell grew well (doubling time=about 2 days) regardless of the presence or absence of SB203580 as shown in FIG. 3 (polygonal line a and polygonal line b), and its S phase cell was about 20% as shown in FIG. 4. The SB203580-untreated senescent cell grew slowly (doubling time=about 6 days) (cf. polygonal line d in FIG. 3), its S phase cell was about 5% (cf. FIG. 4). Although illustrative data are not shown, it showed a morphologically characteristic of a cellular senescence-specific β-galactosidase-positive flat cytoplasm. On the other hand, the SB203580-treated senescent cell showed accelerated growth in comparison with the untreated case (cf. polygonal line c in FIG. 3), the S phase cell shown by 72 hours of bromodeoxyuridine (BrdU) labeling was significantly increased to about 25% (cf. FIG. 4), and it showed a morphologically characteristic in that the cellular senescence-specific β-galactosidase-positive degree was low and the flat cytoplasm became thin, thus resembling the young cell. Based on these results, it was shown that the SB203580 as a compound having p38 protein inhibitory activity partially restarts cell growth of a cell reaching its replicative life span.

Example 2

(1) Preparation of Transformed Cell of the Present Invention

In the example, the transformed cell of the present invention was prepared in accordance with the procedure described as follows, by introducing a human MKK6 gene coding for the human MKK6 protein, or an MKK6EE gene coding for a constitutive active type mutant of the MKK6 (to be referred to as MKK6EE protein hereinafter), into a young cell of the human normal fibroblast WI-38 by a gene introduction method which uses a retrovirus.

In this connection, the MKK6 protein is an MAPK kinase (MAPKK) which phosphorylates and activates p38 protein. Also, the MKK6EE protein is a mutant of the MKK6 protein in which serine at the 207th position (Ser 207) and threonine at the 211th (Thr 211) are respectively substituted with glutamic acid (Glu; E) (*Mol. Cell. Biol.*, 16: 1247-1255, 1996).

The MKK6 gene was obtained by amplifying a DNA fragment of about 1 kbp by a PCR method which uses a plasmid pSRα-MKK6 (*J. Biol. Chem.*, 271: 13675-13679, 1996) as the template and a combination of a forward primer consisting of the nucleotide sequence represented by SEQ ID NO:1 and a reverse primer consisting of the nucleotide sequence represented by SEQ ID NO:2. In this case, the aforementioned PCR was carried out by incubating at 94° C. (5 minutes), repeating a cycle of 94° C. (30 seconds), 52° C. (30 seconds) and 72° C. (1 minute) 15 times and then finally incubating at 72° C. (10 minutes). Also, the MKK6EE gene was obtained by modifying the aforementioned MKK6 gene using a genetic engineering technique in accordance with the conventional method, namely site-specific mutagenesis (*Proc. Natl. Acad. Sci. USA*, 81: 5662-5666, 1984).

Each of the thus obtained MKK6 gene and MKK6EE gene was subcloned into a puromycin-resistant gene-containing retrovirus vector pMXpuro (*Exp. Hematol.*, 24: 324-329, 1996).

The gene introduction by retrovirus was carried out in accordance with a conventionally known method (*Proc. Natl. Acad. Sci. USA*, 92: 9146-9150, 1995). That is, a packaging cell NX cell [4×10$^6$ cells/10 cm dish (*J. Virol.*, 38: 895-905, 1981)] was transfected with 6 μg of a retrovirus DNA containing each gene (or the retrovirus vector pMXpuro as a control). After 48 hours, the culture supernatant was recovered and used as a virus solution.

As the target cell, young cell (42 PD; 5×10$^5$ cells/10 cm dish) of the human normal fibroblast WI-38 was cultured for 8 hours in the virus supernatant to which polybrene (final concentration=8 μg/ml) had been added. The virus supernatant was once removed, and then fresh virus supernatant [containing polybrene (final concentration=8 μg/ml)] was again added, followed by the culturing for 8 hours. Each of the infection-treated cells was cultured for 3 days in DMEM containing puromycin (2.5 μg/ml).

On the 4th day after carrying out the infection, the medium was changed to DMEM containing 2.5% dimethyl sulfoxide (DMSO), followed by the culturing for 6 days. In this case, the medium exchange was carried out every day during the culturing for 6 days. The relative number of cells during these 6 days was measured every other day using a commercially available kit [Cell Counting Kit (WST-1 assay), manufactured. by DOJINDO].

The WST-1 assay is a method to know indirectly degree of cell growth ability with the use of the calorimetric determination of the activity of dehydration reactions wherein intracellular lactate dehydrogenase and the like are related.

Measurement and calculation of the relative cell number were specifically carried out by the following method. That is, 1,000 cells per each well of a 96 well plate were precultured for 24 hours. After adding the WST-1 reagent to the culture medium, the coloring reaction was carried out for 4 hours in a $CO_2$ incubator. After the reaction, measurement was carried out using a plate reader (measuring wave length=450 nm). These were measured on three samples on each of the measuring days (on the 0th, 2nd, 4th and 6th days) during the growth period, and the average values were used as the data of respective measuring days. The relative number of cells of measured values on respective measuring days was calculated by defining the average of measured values on the 0th day as 1. The results are shown in FIG. 5(a).

Figure 5:
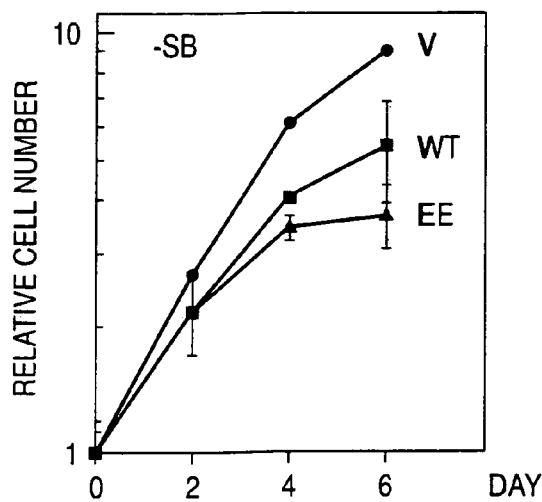
FIG. 5 is a graph showing cell growth curve of the transformed cell of the present invention in the absence [graph (a)] or presence [graph (b)] of a p38 protein inhibitor, SB203580.
Figure 5:
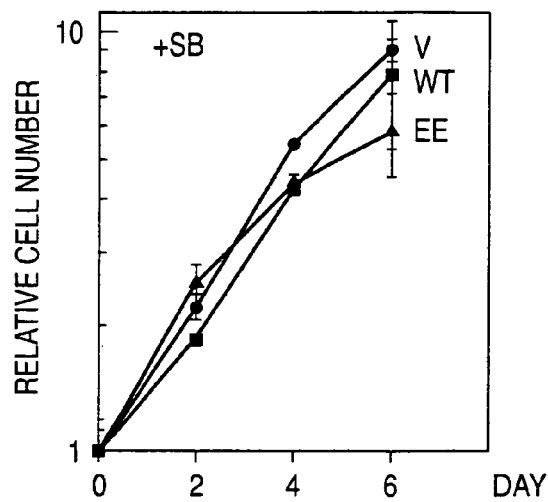

In FIG. 5, the 4th day after carrying out the infection treatment was used as the "0th day". Also, in FIG. 5, the symbol "WT" indicates that it is a result of the MKK6 gene-introduced cell of the present invention, the symbol "EE" indicates that it is a result of the MKK6EE gene-introduced cell of the present invention, and the symbol "V" indicates that it is a result of the vector (retrovirus vector pMXpuro) alone-introduced cell (control).

As shown in FIG. 5(a), cell growth rates of the MKK6-expressing cell (WT) of the present invention and the MKK6EE-expressing cell (EE) of the present invention were significantly reduced on the 4th day, in comparison with the control cell (V) infected with the vector alone. In addition, in the case of the cell (EE) of the present invention expressing the MKK6EE gene, its growth was completely stopped before the cell became confluent.

(2) Effect of p38 Protein Inhibitor on the Transformed Cell of the Present Invention In the example, effect of the p38 protein inhibitor SB203580 on the two species of the transformed cell of the present invention obtained in Example 2(1) was confirmed.

Specifically, the retrovirus infection treatment described in Example 2(1) and culturing of the cells obtained by the treatment described-above were repeated, except that the medium was replaced by DMEM containing 10 μmol//L SB203580 (manufactured. by Sigma) on the 4th day after carrying out the infection treatment. The results are shown in FIG. 5(b).

The symbol "+SB" in FIG. 5(b) indicates that it is a result of the case of adding SB203580 to the medium. In this connection, the symbol "−SB" in FIG. 5(a) indicates that it is a result of the case where SB203580 was not added to the medium.

With regard to the growth inhibitory effect by the MKK6 gene or MKK6EE gene shown in FIG. 5(a), it was inhibited by the p38 protein inhibitor SB203580 as shown in FIG. 5(b).

In addition, although illustrative data were not shown, the SB203580 also showed the anti-aging activity upon a senescent cell (61 PD) of the human normal fibroblast WI-38 cultured in the same manner as in Reference Example 1(1).

(3) Confirmation of Various Aging Indexes in the Transformed Cell of the Present Invention (3-a) Ratio of S Phase Cell by FACS Analysis Using the two species of the transformed cell of the present invention and one species of a control cell wherein the vector alone was introduced, obtained by repeating the same procedure of Example 2(1), the ratio of S phase cell was confirmed by a fluorescence-activated cell sorter (FACS) analysis. As the cells, cells after a culturing period of 6 days, namely the cells of "during 6 days" in FIG. 5, were used.

Specifically, each of the cells after a culturing period of 6 days was subjected to labeling in DMEM medium containing 10 μmol//L bromodeoxyuridine (BrdU) for 4 hours. Next, the cells were fixed with 70% ethanol and treated with 2 mol//L hydrochloric acid for 30 minutes. Subsequently, they were neutralized with 0.1 mol//L sodium borate and then allowed to react with FITC-labeled anti-BrdU antibody (manufactured by BECTON DICKINSON) for 1 hour. After completion of the reaction, the cells were washed with a washing buffer [PBS containing 0.5% Tween 20 and 1% bovine serum albumin (BSA)] and suspended in a PBS solution containing 5 μg/ml ProPidium Iodide (PI). The samples were analyzed by a two dimensional flow cytometry. The results are shown in FIG. 6.

Figure 6:
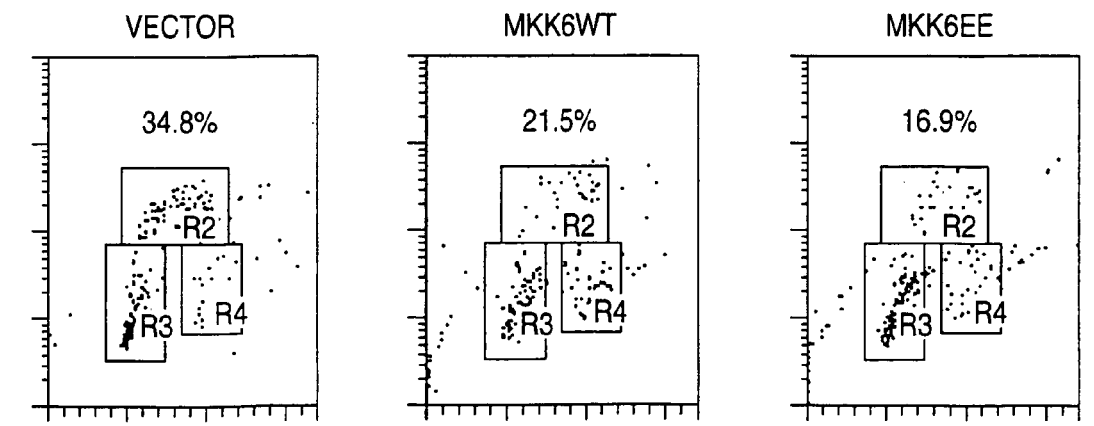
FIG. 6 is a graph showing the ratio of S phase cell in the transformed cell of the present invention, by FACS analysis.

The symbol "Vector" in FIG. 6(a) indicates that it is a result of the vector (retrovirus vector pMXpuro) alone-introduced cell (control), the symbol "MKK6WT" in FIG. 6(b) indicates that it is a result of the MKK6 gene-introduced cell of the present invention, and the symbol "MKK6EE" in FIG. 6(c) indicates that it is a result of the MKK6EE gene-introduced cell of the present invention. Each ordinate in FIG. 6 shows the degree of BrdU staining, and each abscissa shows the degree of PI staining.

As shown in FIG. 6, the ratio of S phase cell in the MKK6-expressing cell (MKK6WT) of the present invention and the MKK6EE-expressing cell (MKK6EE) of the present invention was significantly reduced in comparison with the control cell (Vector) infected with the vector alone.

(3-b) Cellular Senescence-specific β-galactosidase Activity

The procedure described in Reference Example 1(2) was repeated, except that the two species of the transformed cell of the present invention and one species of a control cell wherein the vector alone was introduced, obtained by repeating the same procedure of Example 2(1), (cells after a culturing period of 6 days in each case, namely the cells of "on the 6th day" in FIG. 5) were used. The results are shown in FIG. 7.

The symbol "Vector" in FIG. 7(a) indicates that it is a result of the vector (retrovirus vector pMXpuro) alone-introduced cell (control), the symbol "MKK6WT" in FIG. 7(b) indicates that it is a result of the MKK6 gene-introduced cell of the present invention, and the symbol "MKK6EE" in FIG. 7(c) indicates that it is a result of the MKK6EE gene-introduced cell of the present invention.

As shown in FIG. 7, the MKK6-expressing cell (MKK6WT) of the present invention and the MKK6EE-expressing cell (MKK6EE) of the present invention showed a flat morphology and, what is more, their cellular senescence-specific β-galactosidase activity was considerably increased.

Next, the procedure described in Reference Example 1 (2) was repeated, except that the two species of the transformed cell of the present invention and one species of a control cell wherein the vector alone was introduced, obtained by repeating the same procedure of Example 2(1), (cells after a culturing period of 6 days in each case; SB203580-untreated cells) and the two species of the transformed cell of the present invention and one species of a control cell wherein the vector alone was introduced, obtained by repeating the same procedure of Example 2(2), (cells after a culturing period of 6 days in each case; SB203580-treated cells) were used. Then 200 cells were optionally selected under a microscope from each of independent three samples per each group, and the ratio of β-galactosidase positive cells was calculated by counting the number of β-galactosidase positive cells contained therein. The results are shown in FIG. 8.

Figure 8:
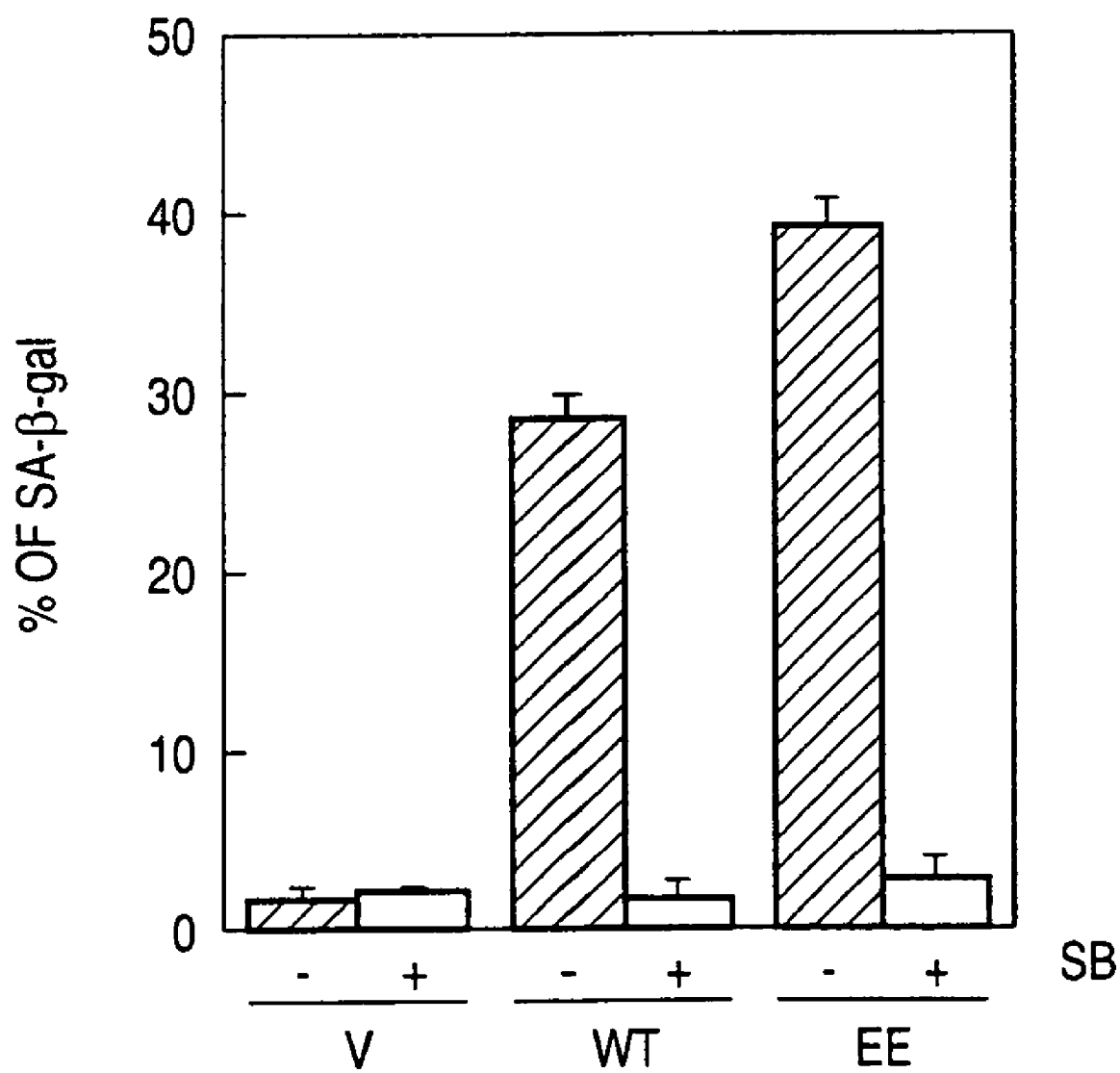
FIG. 8 is a graph showing a result of the determination of β-galactosidase activity in the transformed cell of the present invention.

In FIG. 8, the symbol "V" indicates that it is a result of the vector (retro virus vector pMXpuro) alone-introduced cell (control), the symbol "WT" indicates that it is a result of the MKK6 gene-introduced cell of the present invention, and the symbol "EE" indicates that it is a result of the MKK6EE gene-introduced cell of the present invention. Also, in the "SB" column shown on the abscissa of FIG. 8, the symbol "+" indicates that it is a result of the SB203580-treated cells, and the symbol "−" indicates that it is a result of the SB203580-untreated cells.

As shown in FIG. 8, the increase of the cellular senescence-specific β-galactosidase positive cells is inhibited by SB203580.

(3-c) Phosphorylated State of p38 Protein

The procedure described in Reference Example 1(3) was repeated, except that the two species of the transformed cell of the present invention and one species of a control cell wherein the vector alone was introduced, obtained by repeating the same procedure of Example 2(1), (cells after a culturing period of 6 days in each case) were used, and that an anti-MKK6 antibody (sc-1992; manufactured by Santa Cruz), an anti-p16 antibody (sc-468; manufactured by Santa Cruz), an anti-p21 antibody (sc-817; manufactured by Santa Cruz), an anti-p53 antibody (sc-263; manufactured by Santa Cruz) and an anti-actin antibody (manufactured by Boehringer-Mannheim) were used as the primary antibodies. In this connection, the p16 protein and p21 protein are known proteins as proteins characteristic of senescent cells. Also, actin is a protein which is known to have no difference in its expression quantity between young cells and senescent cells. The results are shown in FIG. 9.

Figure 9:
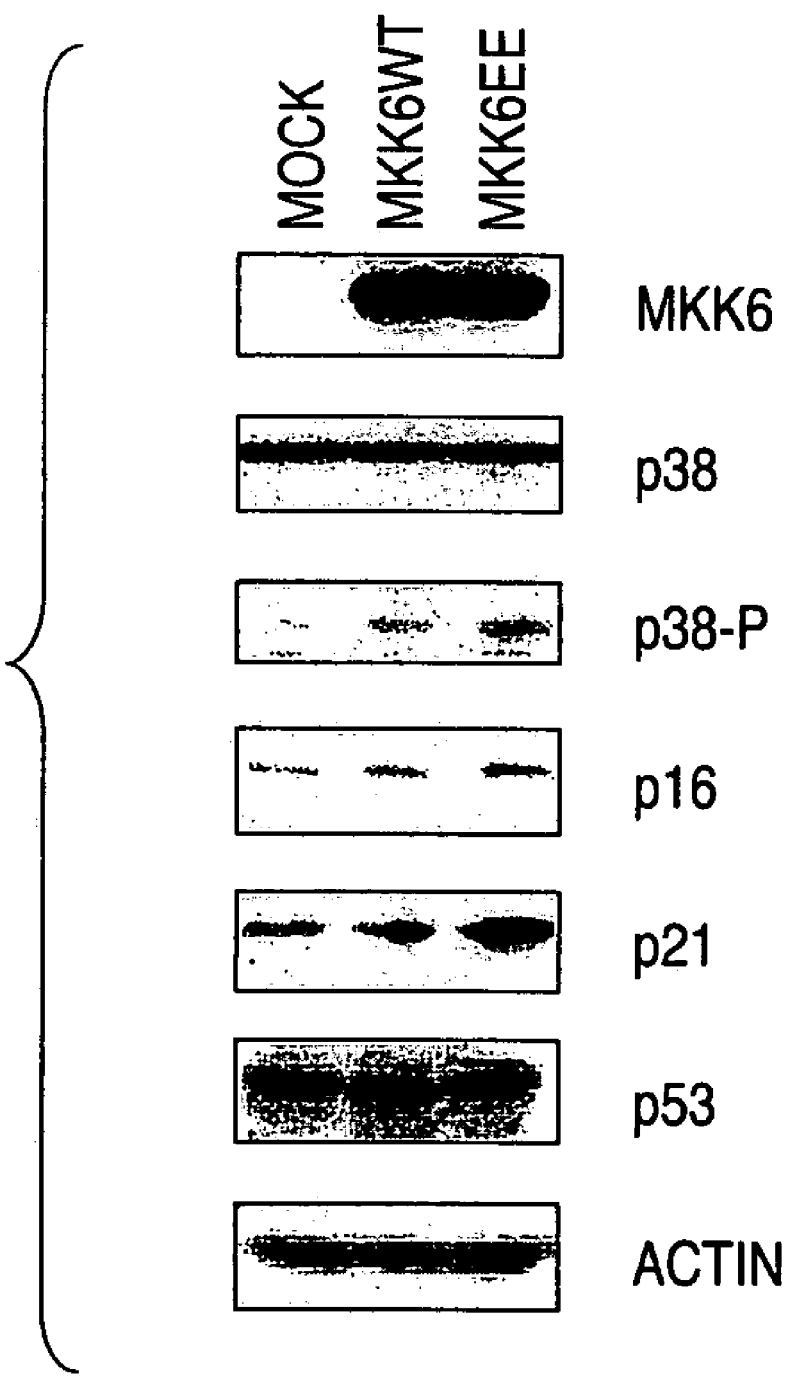
FIG. 9 is a photograph which is substitute for a drawing, showing a result of western blotting of the transformed cell of the present invention.

In FIG. 9, the symbol "mock" indicates that it is a result of the vector (retrovirus vector pMXpuro) alone-introduced cell (control), the symbol "MKK6WT" indicates that it is a result of the MKK6 gene-introduced cell of the present invention, and the symbol "MKK6EE" indicates that it is a result of the MKK6EE gene-introduced cell of the present invention.

As shown in FIG. 9, a large amount of the MKK6 protein was expressed in the MKK6 or MKK6EE gene-introduced cell in comparison with the control. While expressed amount of the total p38 protein did not vary among the three species of cells, expressed amount of the active type p38 protein significantly increased in the MKK6 gene-introduced cell and markedly increased in the MKK6EE gene-introduced cell in comparison with the control. In addition, expressed amount of each of the senescent cell-specific p16 protein and p21 protein increased in the MKK6 or MKK6EE gene-introduced cell. It was found based on these results that cellular senescence is directly induced into young cells by the activation of p38 protein.

Example 3

It was already reported that human normal fibroblast rapidly shows a cellular senescence phenotype by the forced expression of activated Ras (*Cell,* 88: 1593-602, 1997). It was shown that this process is induced via the classical MAPK, namely Raf-Mek-Erk, which is in the downstream of Ras (*Genes Dev.,* 12: 3008-3019, 1998, *Genes Dev.,* 12: 2997-3007, 1998). By the use of this, Zhu et al. have reported a system for inducing cellular senescence by activating Raf with estrogen or tamoxifen (*Genes Dev.,* 12: 2997-3007, 1998). This is a result of fusing an estrogen receptor gene with a sequence coding for the kinase region of activated Raf gene.

(1) In accordance with the aforementioned method, induction of cellular senescence was tested by carrying out gene transfer into the WI-38 cell and thereby constructing a system which can induce cellular senescence by the administration of tamoxifen.

Figure 10:
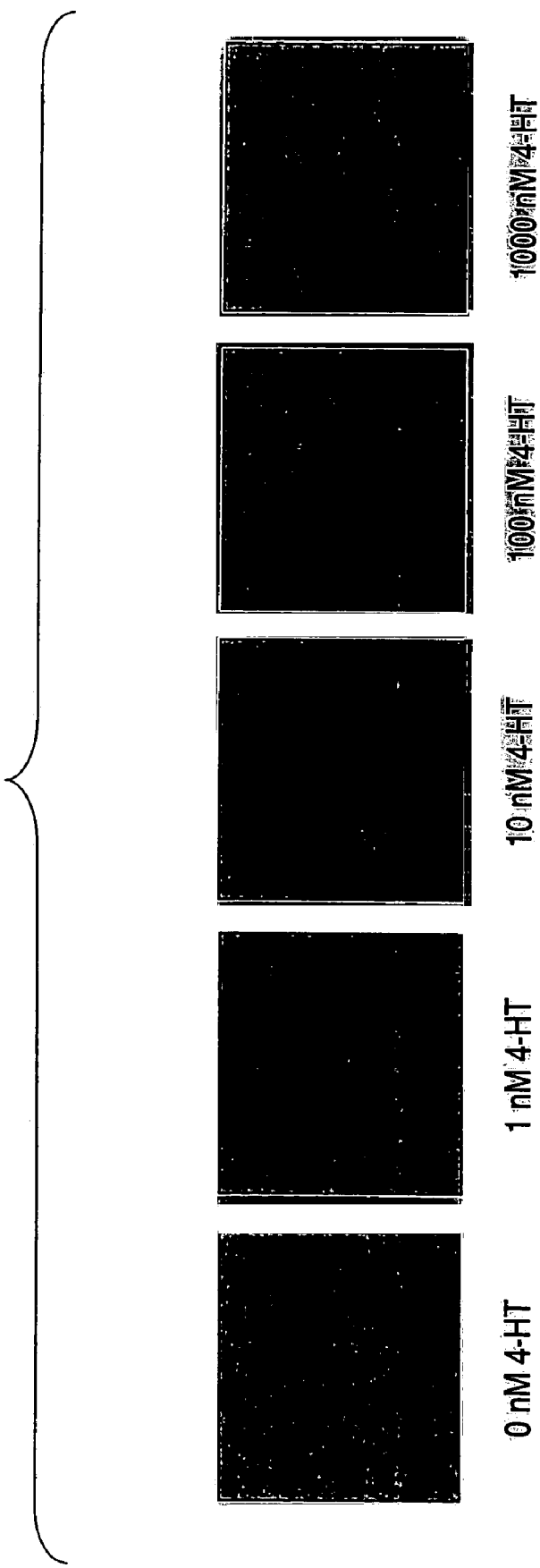
FIG. 10 is a photomicrograph which is a substitute for a drawing, showing morphological changes of the transformed cell of the present invention by varied concentration of added tamoxifen.
Figure 11:
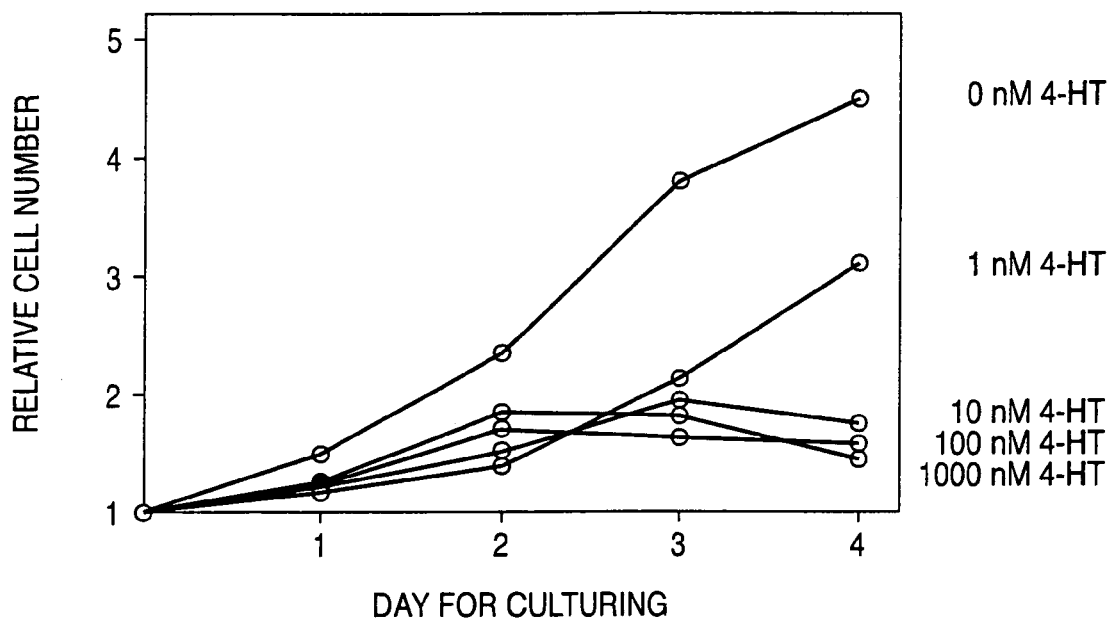
FIG. 11 is a graph showing variation per day in the growth ratio of the transformed cell of the present invention by varied concentration of added tamoxifen.

The results are shown in FIG. 10 and FIG. 11. By the administration of 1 nM or more of tamoxifen, termination of cell growth and increase of cellular senescence-specific β-galactosidase positive cell were observed, there by confirming that the cellular senescence was induced. FIG. 10 shows the changes in the morphology of cells by varied administration concentration of tamoxifen (4-HT), and FIG. 11 shows a relationship between concentration of administered tamoxifen (4-HT) and the relative number of cells wherein the initial number of cells is defined as 1.

(2) Using the system constructed in (1), activation of Raf was induced by 10 nM of tamoxifen, and by simultaneously adding 25 µM of PD98059 (Mek inhibitor) and SB203580 (p38 inhibitor), their effects on the Raf-induced cellular senescence induction was observed. The results are shown in FIG. 12, FIG. 13, FIG. 14 and FIG. 15.

Figure 12:
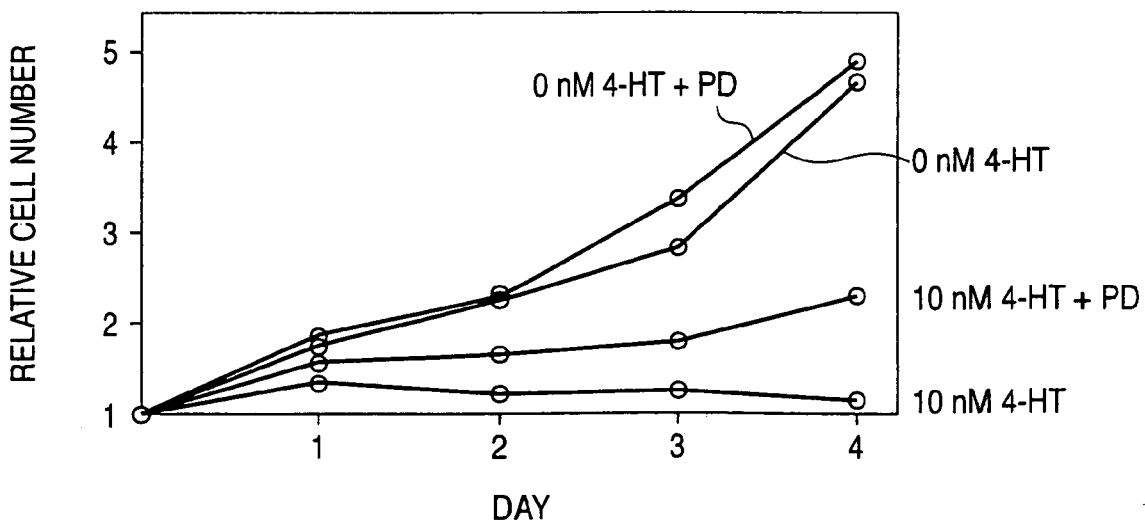
FIG. 12 is a graph showing variation per day in the growth ratio of the transformed cell of the present invention in the presence or absence of added tamoxifen and PD98059.

FIG. 12 shows the ratio of cell growth in respective cells after induction of the activated Raf. In FIG. 12, tamoxifen is shown by a symbol "4-HT", and the 25 µM PD98059-administered system is shown by a symbol "+PD".

Figure 13:
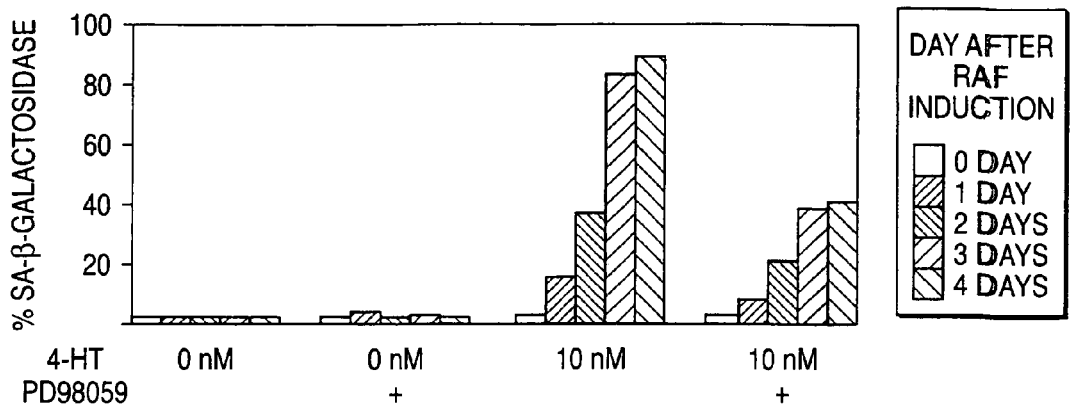
FIG. 13 is a graph showing a result of the quantitation of β-galactosidase in the transformed cell of the present invention in the presence or absence of added tamoxifen and PD98059.

FIG. 13 shows the ratio of β-galactosidase positive cell in respective cells after induction of the activated Raf. In FIG. 13, tamoxifen is shown by a symbol "4-HT", and the 25 µM PD98059-administered system is shown by a symbol "+".

Figure 14:
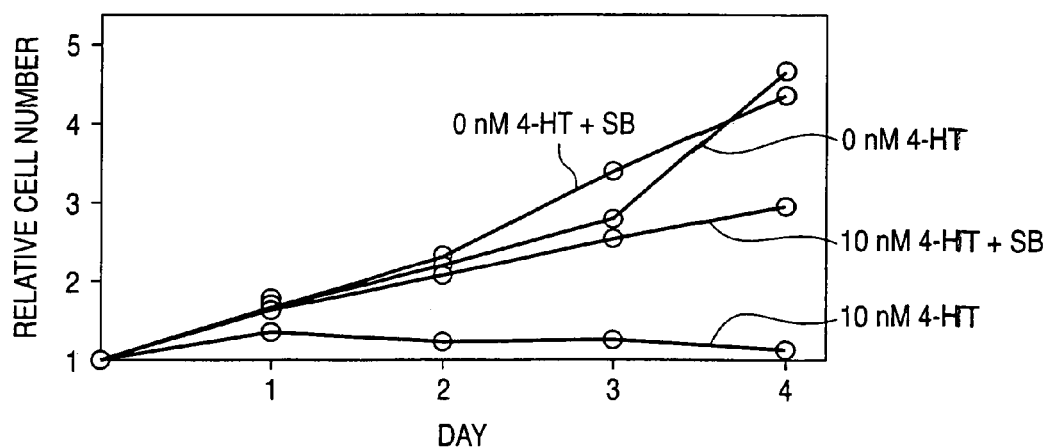
FIG. 14 is a graph showing variation per day in the growth ratio of the transformed cell of the present invention in the presence or absence of added tamoxifen and SB203580.

FIG. 14 shows the ratio of cell growth in respective cells after induction of the activated Raf. In FIG. 14, tamoxifen is shown by a symbol "4-HT", and the 25 µM SB203580-administered system is shown by a symbol "+SB".

Figure 15:
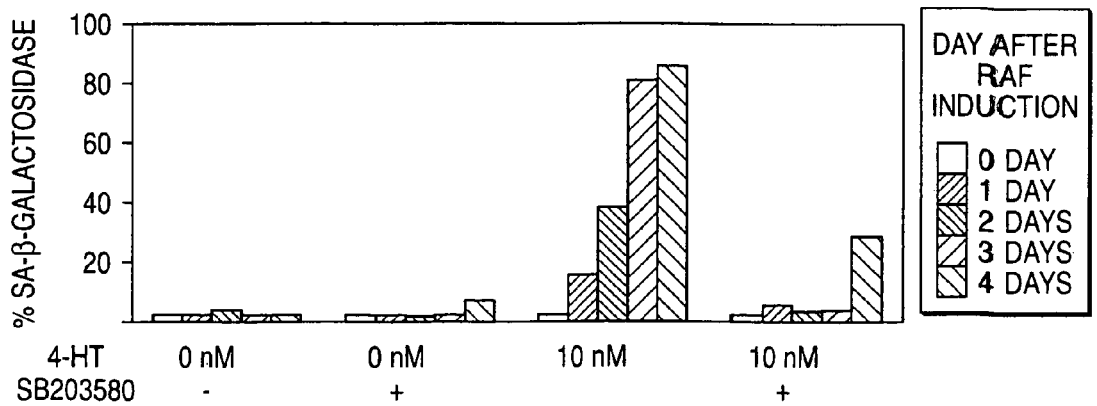
FIG. 15 is a graph showing a result of the quantitation of β-galactosidase in the transformed cell of the present invention in the presence or absence of added tamoxifen and SB203580.

FIG. 15 shows the ratio of β-galactosidase positive cell in respective cells after induction of the activated Raf. In FIG. 15, tamoxifen is shown by a symbol "4-HT", and the 25 µM SB203580-administered system is shown by a symbol "+".

PD98059 partially inhibited the termination of cell growth and increase of cellular senescence-specific β-galactosidase positive cell induced by the activation of Raf. However, SB203580 inhibited the termination of cell growth and increase of cellular senescence-specific β-galactosidase positive cell induced by the activation of Raf, more strongly than the PD98059. It was clarified by this information that both of the classical MAPK and a stress-inducing MAPK p38 are concerned in the cellular senescence induced by the activation of Raf, but the concern of p38 is particularly large.

INDUSTRIAL APPLICABILITY

The transformed cell of the present invention is a cell useful for constructing the screening system of the present invention, and, according to the screening method of the present invention, a substance effective as an anti-aging agent can be screened. In addition, a compound selected by the screening method of the present invention is useful as an anti-aging agent.

The invention claimed is:

1. An isolated senescent cell prepared by introducing and expressing an exogenous gene in a juvenile, non-transformed, mammalian cell;
   wherein said gene codes for a protein that directly phosphorylates p38 protein.

2. The isolated senescent cell of claim 1, wherein said juvenile, non-transformed, mammalian cell is a human, monkey, mouse, rat or hamster cell.

3. The isolated senescent cell of claim 2, wherein said juvenile, non-transformed, mammalian cell is a human cell.

4. The isolated senescent cell of claim 1, wherein said juvenile, non-transformed, mammalian cell is a fibroblast, a keratinocyte, a mammary gland epithelial cell, or a vascular endothelial cell.

5. The isolated senescent cell of claim 4, wherein said juvenile, non-transformed, mammalian cell is a fibroblast cell.

6. The isolated senescent cell of claim 5, wherein said juvenile, non-transformed, mammalian cell is a human fibroblast cell.

7. The isolated senescent cell of claim 1, wherein said juvenile, non-transformed, mammalian cell is a cell of 0 to 50 population doublings (PD).

8. The isolated senescent cell of claim 1, wherein said protein that directly phosphorylates p38 protein is selected from the group consisting of: MKK6 protein or MKK3 protein.

9. The isolated senescent cell of claim 1, wherein said exogenous gene is introduced in said juvenile, non-transformed, mammalian cell using a retrovirus, an adenovirus, DEAE-dextran method, calcium phosphate-DNA precipitation method, transfection reagent or electroporation.

10. A method for preparing a senescent cell, comprising:
    introducing and expressing an exogenous gene in a juvenile, non-transformed, mammalian cell;
    wherein said gene codes for a protein that directly phosphorylates p38 protein.

* * * * *